United States Patent
Saito et al.

(10) Patent No.: US 11,858,881 B2
(45) Date of Patent: Jan. 2, 2024

(54) METHOD FOR PURIFYING NITRILE SOLVENT

(71) Applicant: NIPPON SODA CO., LTD., Tokyo (JP)

(72) Inventors: Shota Saito, Takaoka (JP); Ryoji Wada, Takaoka (JP); Keiichiro Matsuda, Takaoka (JP); Ryoyo Nakashima, Takaoka (JP); Fuminori Komatsu, Takaoka (JP)

(73) Assignee: NIPPON SODA CO., LTD., Tokyo (JP)

( * ) Notice: Subject to any disclaimer, the term of this patent is extended or adjusted under 35 U.S.C. 154(b) by 653 days.

(21) Appl. No.: 16/975,317

(22) PCT Filed: Feb. 26, 2019

(86) PCT No.: PCT/JP2019/007306
§ 371 (c)(1),
(2) Date: Aug. 24, 2020

(87) PCT Pub. No.: WO2019/167940
PCT Pub. Date: Sep. 6, 2019

(65) Prior Publication Data
US 2020/0399207 A1 Dec. 24, 2020

(30) Foreign Application Priority Data
Feb. 27, 2018 (JP) .................. 2018-033238

(51) Int. Cl.
C07C 253/34 (2006.01)
B01D 3/40 (2006.01)
C07C 255/08 (2006.01)

(52) U.S. Cl.
CPC .............. *C07C 253/34* (2013.01); *B01D 3/40* (2013.01); *C07C 255/08* (2013.01)

(58) Field of Classification Search
None
See application file for complete search history.

(56) References Cited

U.S. PATENT DOCUMENTS

| 2,242,309 A | 5/1941 | Lazier et al. |
| 3,725,459 A | 4/1973 | Yamada et al. |

FOREIGN PATENT DOCUMENTS

| CN | 105085318 A | 11/2015 |
| DE | 1150062 B | 6/1963 |
| EP | 1 882 682 A1 | 1/2008 |
| GB | 731458 A | 6/1955 |
| JP | S46-3047 B1 | 1/1971 |
| JP | S46-37566 B1 | 11/1971 |
| JP | S48-530 A | 1/1973 |
| JP | S48-7617 B1 | 3/1973 |
| JP | S48-22421 A | 3/1973 |
| JP | S49-35248 B1 | 9/1974 |
| JP | S49-48408 B1 | 12/1974 |
| JP | S51-32518 A | 3/1976 |
| JP | S51-44928 B1 | 12/1976 |
| JP | S52-68118 A | 6/1977 |
| JP | S57-62247 A | 4/1982 |
| JP | H05-25112 A | 2/1993 |
| JP | H05-32605 A | 2/1993 |
| JP | H06-329610 A | 11/1994 |
| JP | H08-12640 A | 1/1996 |
| WO | 2006/121081 A1 | 11/2006 |

OTHER PUBLICATIONS

Oct. 22, 2021 Extended European Search Report issued in European Patent Application 19760953.0.
May 21, 2019 International Search Report issued in International Patent Application No. PCT/JP2019/007306.
Jul. 19, 2022 Office Action issued in Taiwanese Patent Application No. 108106813.

*Primary Examiner* — Joseph R Kosack
(74) *Attorney, Agent, or Firm* — Oliff PLC

(57) ABSTRACT

A method for manufacturing a higher purity nitrile solvent by purifying a nitrile solvent containing an impurity, e.g an imine. The nitrile solvent may contain an imine and a conjugated diene, a carbonyl compound, or a high-boiling material as impurities. A method for purifying a nitrile solvent, such as isobutyronitrile, including bringing nitrile solvent containing an imine, e.g., as an impurity, into contact with an acidic aqueous solution having a pH of 3 or less, such as hydrochloric acid; bringing the nitrile solvent having been contacted with acidic aqueous solution into contact with an aqueous sodium hydrogen sulfite solution; bringing the nitrile solvent having been contacted with the aqueous sodium hydrogen sulfite solution into contact with an alkaline aqueous solution, such as an aqueous sodium hydroxide solution; and distilling the nitrile solvent having been contacted with the alkaline aqueous solution.

9 Claims, No Drawings

METHOD FOR PURIFYING NITRILE SOLVENT

TECHNICAL FIELD

The present invention relates to a method for purifying a nitrile solvent. The present application claims priority to Japanese Patent Application No. 2018-33238, filed Feb. 27, 2018, the entirety of which is hereby incorporated by reference.

BACKGROUND ART

Nitrile solvents may contain impurities. Since impurities may cause various problems, a variety of purification methods have been proposed.

For example, patent document 1 discloses a method for manufacturing methacrylonitrile, which includes bringing a gas generated by ammoxidation reaction of isobutylene or t-butyl alcohol into contact with an aqueous sodium hydrogen sulfite solution at a pH of 5 to 9 and a temperature of 80° C. or less and separating and removing methacrolein contained in the gas.

Patent document 2 discloses a method for purifying acetonitrile characterized in that acetonitrile that is by-produced in ammoxidation of propylene is brought into contact with an aqueous solution of an alkali metal salt or alkaline earth metal salt of hypochlorous acid. Patent document 2 describes that it is preferable to use in this contact treatment a mineral acid, such as hydrochloric acid, sulfuric acid, nitric acid, or phosphoric acid, together.

Patent document 3 discloses that acrolein being an impurity is removed by adding acetylacetone and dimethylaminoethanol to acrylonitrile, heating them at 50° C., then adding an aqueous ferric chloride solution thereto, subsequently cooling the solution to ordinary temperature, and performing rectification.

Patent document 4 discloses a method for manufacturing high-purity acetonitrile characterized in that water-containing crude acetonitrile is mixed with an alkali, the mixture is separated into an acetonitrile phase and an aqueous phase, the aqueous phase is removed, the resulting acetonitrile phase is subjected to a distillation process to obtain purified acetonitrile, and the resulting purified acetonitrile is applied to a cation exchange resin to obtain high-purity acetonitrile.

Patent document 5 discloses a method for purifying crude acetonitrile characterized in that a first step of bringing crude acetonitrile as a raw material into contact with nascent oxygen and a second step of bringing the acetonitrile that has undergone the first step into contact with one or more materials selected from solid bases and adsorbents are performed in this order to purify the crude acetonitrile.

Patent document 6 discloses a method for purifying acetonitrile characterized in that crude acetonitrile by-produced by ammoxidation reaction of propylene or isobutylene in the presence of a catalyst is brought into contact with a gas containing ozone, and subsequently, neutralization with a basic material and then distillation are performed to obtain acetonitrile that does not absorb ultraviolet light having a wavelength of 200 to 350 nm.

Patent document 7 discloses a method for purifying acetonitrile characterized in that crude acetonitrile by-produced by ammoxidation reaction of propylene or isobutylene in the presence of a catalyst is brought into contact with sulfuric acid, the sulfuric acid content was then separated, and, then, contact with a gas containing ozone and then distillation are performed to obtain acetonitrile that does not absorb ultraviolet light having a wavelength of 200 to 350 nm.

Patent document 8 discloses a method for purifying crude acetonitrile characterized by purification of crude acetonitrile consisting of a first step of bringing crude acetonitrile as a raw material into contact with nascent oxygen, a second step of bringing the acetonitrile that has undergone the first step into contact with one or more materials selected from basic materials and adsorbents, a third step of separating and removing permanganic acid reducing materials contained in the acetonitrile that has undergone the second step, and a fourth step of separating and removing low-boiling compounds and high-boiling compounds contained in the acetonitrile that has undergone the third step. In patent document 8, as the permanganic acid reducing material, iron chloride, sodium hydrogen sulfite, or the like is exemplified.

PRIOR ART DOCUMENTS

Patent Documents

Patent document 1: Japanese unexamined Patent Application Publication No. 57-62247
Patent document 2: Japanese unexamined Patent Application Publication No. 51-32518
Patent document 3: Japanese unexamined Patent Application Publication No. 52-68118
Patent document 4: International Publication No. WO 2006/121081 A1
Patent document 5: Japanese unexamined Patent Application Publication No. 6-329610
Patent document 6: Japanese unexamined Patent Application Publication No. 5-25112
Patent document 7: Japanese unexamined Patent Application Publication No. 5-32605
Patent document 8: Japanese unexamined Patent Application Publication No. 8-12640

SUMMARY OF THE INVENTION

Object to be Solved by the Invention

The use of nitrile solvents is widely spreading in advanced technical fields, such as solvents for organic synthesis reactions, raw materials for agricultural chemicals and pharmaceuticals, and also electrolytes for secondary batteries, solvents for synthesizing organic EL materials, and cleansing solutions for electronic parts. Accordingly, an ultra-high purity nitrile solvent is needed. Existing technologies have focused on removal of carbonyl compounds, such as aldehyde, and have not considered removal of imines.

It is an object of the present invention to provide a method for manufacturing a higher purity nitrile solvent by purifying a nitrile solvent containing an imine, etc., as an impurity. In particular, it is an object to provide a method for manufacturing a higher purity nitrile solvent by purifying a nitrile solvent containing an imine and a conjugated diene, a carbonyl compound, or a high-boiling material as impurities.

Means to Solve the Object

As a result of investigations for solving the above problems, the present invention including the following embodiments has been found.
[1] A method for purifying a nitrile solvent, comprising:

bringing the nitrile solvent containing an impurity into contact with an acidic aqueous solution having a pH of 3 or less;

bringing the nitrile solvent having been contacted with the acidic aqueous solution into contact with an aqueous sodium hydrogen sulfite solution; and bringing the nitrile solvent having been contacted with the aqueous sodium hydrogen sulfite solution into contact with an alkaline aqueous solution.

[2] The method for purifying a nitrile solvent according to [1], further comprising bringing the nitrile solvent containing an impurity, the nitrile solvent having been contacted with the acidic aqueous solution, the nitrile solvent having been contacted with the aqueous sodium hydrogen sulfite solution, or the nitrile solvent having been contacted with the alkaline aqueous solution, into contact with an oxidizing agent.

[3] The method for purifying a nitrile solvent according to [1] or [2], further comprising distilling the nitrile solvent having been contacted with the alkaline aqueous solution or the nitrile solvent having been contacted with the oxidizing agent.

[4] The method for purifying a nitrile solvent according to any one of [1] to [3], wherein the acidic aqueous solution is hydrochloric acid.

[5] The method for purifying a nitrile solvent according to any one of [1] to [4], wherein the alkaline aqueous solution is an aqueous sodium hydroxide solution.

[6] The method for purifying a nitrile solvent according to any one of [1] to [5], wherein the nitrile solvent is isobutyronitrile.

[7] A method for purifying a nitrile solvent, comprising:

bringing a nitrile solvent containing an imine as an impurity into contact with an acidic aqueous solution having a pH of 3 or less to convert the imine being the impurity into a carbonyl compound; and then subjecting the nitrile solvent having been contacted with the acidic aqueous solution to a treatment for removing the carbonyl compound.

Effects of the Invention

According to the purification method of the present invention, a high purity nitrile solvent can be obtained from a nitrile solvent containing an imine, etc., as an impurity. According to the purification method of a preferred embodiment of the present invention, a high purity nitrile solvent can be obtained from a nitrile solvent containing an imine and a conjugated diene, a carbonyl compound, or a high-boiling material as impurities.

MODE OF CARRYING OUT THE INVENTION

The method for purifying a nitrile solvent of the present invention includes performing contact treatment A, contact treatment B, and contact treatment C in this order. A preferred method for purifying a nitrile solvent of the present invention further includes performing contact treatment D and/or distillation treatment.

The nitrile solvent as a subject of the purification method of the present invention is an organic solvent having a cyano group (—CN) in the molecule and contains impurities. The nitrile solvent that is used in the present invention is preferably hydrophobic. Here, the term "hydrophobic" means that the solvent is separated into an aqueous phase and a nitrile solvent phase when left to stand at ordinary temperature.

As the nitrile solvent, a saturated aliphatic nitrile, such as propionitrile, butyronitrile, isobutyronitrile, or valeronitrile, an aromatic nitrile, such as benzonitrile, o-tolunitrile, m-tolunitrile, or p-tolunitrile, or the like may be exemplified. Among these nitrile solvents, a saturated aliphatic nitrile and an aromatic nitrile are preferable.

The purification method of the present invention may be preferably applied to a nitrile solvent containing an imine as an impurity and may be more preferably applied to a nitrile solvent containing an imine and a conjugated diene, a carbonyl compound, and/or a high-boiling material as impurities.

As the imine that is an impurity contained in the nitrile solvent, for example, a compound of formula (I) may be exemplified.

(I)

In the formula (I), $R^1$ to $R^3$ each represent a hydrogen atom or an organic group.

As the conjugated diene that is an impurity contained in the nitrile solvent, for example, a compound of formula (II) may be exemplified.

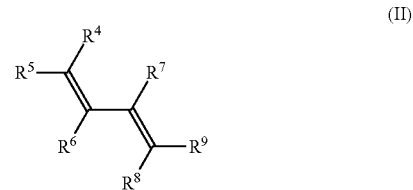

(II)

In the formula (II), $R^4$ to $R^9$ each represent a hydrogen atom or an organic group, and $R^5$ and $R^6$ may be linked to form a ring.

As the carbonyl compound that is an impurity contained in the nitrile solvent, a ketone and an aldehyde may be exemplified.

The high-boiling material that is an impurity contained in the nitrile solvent is a material other than the above-mentioned imine, conjugated diene, and carbonyl compound and having a boiling point higher than the boiling point of the nitrile solvent.

(Contact Treatment A)

As the acidic aqueous solution that is used in the contact treatment A, for example, an aqueous solution of a mineral acid, such as hydrochloric acid (aqueous hydrogen chloride solution), an aqueous sulfuric acid solution, or an aqueous nitric acid solution, may be exemplified. Among these acidic aqueous solutions, hydrochloric acid is preferable. The pH (20° C.) of the acidic aqueous solution is usually 3 or less, and preferably a pH of, for example, 2.9 or less, 2.8 or less, 2.7 or less, 2.6 or less, 2.5 or less, 2.4 or less, 2.3 or less, 2.2 or less, 2.1 or less, 2.0 or less, 1.9 or less, 1.8 or less, 1.7 or less, 1.6 or less, or 1.5 or less may be selected.

The amount of the acidic aqueous solution to be brought into contact is not particularly limited, but an amount of, for example, 1 to 500 wt %, 1 to 400 wt %, 1 to 300 wt %, 1 to 200 wt %, or 1 to 100 wt % with respect to the total weight of the nitrile solvent may be selected.

The method for bringing a nitrile solvent into contact with an acidic aqueous solution is not particularly limited. For example, a method in which a nitrile solvent and an acidic aqueous solution are placed in a batch extractor and stirred or a method in which a nitrile solvent and an acidic aqueous solution are brought into counterflow contact with each other in a continuous extractor may be exemplified. The temperature when a nitrile solvent is brought into contact with an acidic aqueous solution is not particularly limited, but a temperature of, for example, 0° C. to 100° C., 0° C. to 90° C., 0° C. to 80° C., 0° C. to 70° C., 0° C. to 60° C., or 0° C. to 50° C. may be selected.

The imine that is an impurity contained in a nitrile solvent is decomposed into corresponding carbonyl compound and primary amine by the contact treatment with an acidic aqueous solution.

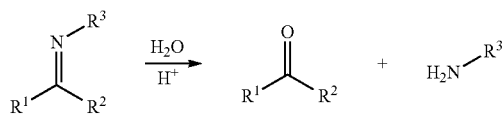

The primary amine is more soluble in the acidic aqueous solution phase than in the nitrile solvent phase. Therefore, the primary amine can be removed from the nitrile solvent by separating the acidic aqueous solution phase from the nitrile solvent phase. Consequently, the carbonyl compound remains as an impurity in the nitrile solvent subjected to the contact treatment A.

(Contact Treatment B)

The aqueous sodium hydrogen sulfite solution that is used in the contact treatment B is not particularly limited by the concentration thereof, but a concentration of, for example, 1 wt % to solubility, 5 wt % to solubility, wt % to solubility, 15 wt % to solubility, 20 wt % to solubility, 25 wt % to solubility, 30 wt % to solubility, or wt % to 35 wt % may be selected. Incidentally, the solubility of sodium hydrogen sulfite (NaHSO$_3$) in water at 25° C. is about 43 to 44 wt %, and the pH of an aqueous sodium hydrogen sulfite solution at 20° C. is preferably higher than 3.0 and more preferably 3.5 to 5.0.

The amount of the aqueous sodium hydrogen sulfite solution to be brought into contact is not particularly limited, but an amount of, for example, 1 to 500 wt %, 1 to 400 wt %, 1 to 300 wt %, 1 to 200 wt %, or 1 to 100 wt % with respect to the total weight of the nitrile solvent may be selected.

The method for bringing a nitrile solvent into contact with an aqueous sodium hydrogen sulfite solution is not particularly limited. For example, a method in which a nitrile solvent and an aqueous sodium hydrogen sulfite solution are placed in a batch extractor and stirred or a method in which a nitrile solvent and an aqueous sodium hydrogen sulfite solution are brought into counterflow contact with each other in a continuous extractor may be exemplified. The temperature when a nitrile solvent and an aqueous sodium hydrogen sulfite solution are brought into contact with each other is not particularly limited, but a temperature of, for example, 0° C. to 100° C., 0° C. to 90° C., 0° C. to 80° C., 0° C. to 70° C., 0° C. to 60° C., or 0° C. to 50° C. may be selected.

The carbonyl compound that is an impurity contained in the nitrile solvent is converted into corresponding α-hydroxysulfonic acid compound by the contact treatment with an aqueous sodium hydrogen sulfite solution.

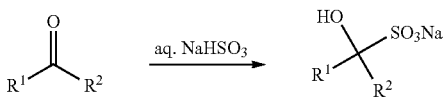

The α-hydroxysulfonic acid compound is more soluble in the aqueous sodium hydrogen sulfite solution phase than in the nitrile solvent phase. Therefore, the α-hydroxysulfonic acid compound (i.e., carbonyl compound) can be removed from the nitrile solvent by separating the aqueous sodium hydrogen sulfite solution phase from the nitrile solvent phase. Thus, an imine being an impurity can be removed.

Instead of the contact treatment B, known treatment for removing a carbonyl compound, such as aldehyde, from a nitrile compound may be performed. For example, a treatment method including removal of aldehyde or the like being impurities in nitrile with an ion exchange resin (see, for example, Japanese unexamined Patent Application Publication Nos. 2000-16978, 58-134063, 10-7638, and 54-151915 and International Publication No. WO 2006/121081 A) or a treatment method including addition of acetylacetone and dimethylaminoethanol to acrylonitrile, heating at 50° C., subsequent addition of an aqueous ferric chloride solution, subsequent cooling to ordinary temperature, and rectification (see, for example, Japanese unexamined Patent Application Publication No. 52-68118) may be exemplified.

(Contact Treatment C)

As the alkaline aqueous solution that is used in the contact treatment C, an aqueous alkali metal hydroxide solution, such as an aqueous sodium hydroxide solution or an aqueous potassium hydroxide solution, an aqueous alkaline-earth metal hydroxide solution, such as an aqueous calcium hydroxide solution or an aqueous strontium hydroxide solution, aqueous ammonia, an aqueous methylamine solution, or the like may be exemplified. Among these alkaline aqueous solutions, an aqueous sodium hydroxide solution is preferable. The concentration of the alkaline aqueous solution is not particularly limited, but a concentration of, for example, 1 wt % to solubility, wt % to solubility, 10 wt % to solubility, 15 wt % to solubility, 20 wt % to solubility, 25 wt % to solubility, 30 wt % to solubility, or 30 wt % to 35 wt % may be selected. Incidentally, the solubility of sodium hydroxide in water at 20° C. is about 109 g/100 mL, and the solubility of potassium hydroxide in water at 25° C. is about 110 g/100 mL.

The amount of the alkaline aqueous solution to be brought into contact is not particularly limited, but an amount of, for example, 1 to 500 wt %, 1 to 400 wt %, 1 to 300 wt %, 1 to 200 wt %, or 1 to 100 wt % with respect to the total weight of the nitrile solvent may be selected.

The method for bringing a nitrile solvent into contact with an alkaline aqueous solution is not particularly limited. For example, a method in which a nitrile solvent and an alkaline aqueous solution are placed in a batch extractor and stirred or a method in which a nitrile solvent and an alkaline aqueous solution are brought into counterflow contact with each other in a continuous extractor may be exemplified. The temperature when a nitrile solvent and an alkaline aqueous solution are brought into contact with each other is not particularly limited, but a temperature of, for example, 0° C. to 100° C., 0° C. to 90° C., 0° C. to 80° C., 0° C. to 70° C., 0° C. to 60° C., or 0° C. to 50° C. may be selected.

The contact with an alkaline aqueous solution neutralizes the acidic material that is an impurity contained in the nitrile solvent and the acidic materials added in the contact treatment A and B to convert them into corresponding salts. The salts are more soluble in the alkaline aqueous solution phase than in the nitrile solvent phase. Therefore, the salts (i.e., acidic materials) can be removed from the nitrile solvent by separating the alkaline aqueous solution phase from the nitrile solvent phase.

(Contact Treatment D)

As the oxidizing agent that is used in the contact treatment D, for example, an aqueous sodium hypochlorite solution (antiformin), hydrogen peroxide, oxygen, air, or ozone may be exemplified. Among these oxidizing agents, oxygen and air are preferable because of ease of handling.

The contact treatment D may be subjected to a nitrile solvent containing impurities before being subjected to the contact treatment A, a nitrile solvent having been contacted with an acidic aqueous solution and before being subjected to the contact treatment B, a nitrile solvent having been contacted with an aqueous sodium hydrogen sulfite solution and before being subjected to the contact treatment C, or a nitrile solvent having been contacted with an alkaline aqueous solution by being subjected to the contact treatment C.

The method for bringing a nitrile solvent into contact with an oxidizing agent is not particularly limited. For example, a method in which a gaseous oxidizing agent, such as oxygen, air, or ozone, is bubbled through a nitrile solvent, a method in which a gaseous oxidizing agent and a nitrile solvent are brought into counterflow contact with each other in a gas absorption column, a method in which a liquid oxidizing agent, such as an aqueous sodium hypochlorite solution (antiformin) or hydrogen peroxide, is added to a nitrile solvent and the mixture is stirred, or a method in which a nitrile solvent is added to a liquid oxidizing agent and the mixture is stirred may be exemplified.

A conjugated diene or the like being an impurity contained in a nitrile solvent is oxidized by bringing the nitrile solvent into contact with an oxidizing agent. From the viewpoint of accelerating the oxidation of the conjugated diene, it is preferable to perform the contact treatment D using a gaseous oxidizing agent in the presence of an aqueous sodium hydrogen sulfite solution. The product obtained by oxidation of a conjugated diene can be removed from the nitrile solvent by the contact treatment with an acidic aqueous solution, the contact treatment with an aqueous sodium hydrogen sulfite solution, or the contact treatment with an alkaline aqueous solution, or the distillation treatment described below.

(Distillation Treatment)

The distillation treatment is preferably performed after the contact treatment C or the contact treatment D. The distillation treatment may be performed by a known method. In the distillation treatment, the nitrile solvent is evaporated, and high-boiling materials, such as N-isobutylformamide, can be separated as a residue.

EXAMPLES

Subsequently, the present invention will be more specifically described by showing an Example, but the technical scope of the present invention is not limited to the example.

Example 1

Crude isobutyronitrile containing, as impurities, 2454 ppm of N-isobutyl-2-methylpropane-1-imine, 37 ppm of isobutyl aldehyde, 8 ppm of 2,5-dimethylhexa-2,4-diene, and 220 ppm of N-isobutylformamide was prepared.

To a 5-L four-necked flask, 2567 mL of the crude isobutyronitrile and 513 mL of water were added. The pH of the aqueous phase thereof was adjusted to 1.9 with 35% hydrochloric acid. Then, the mixture was stirred at 23° C. for 0.5 hours. The liquid was then left to stand for separating into an isobutyronitrile phase and an aqueous phase, and the aqueous phase was removed (contact treatment A).

To the isobutyronitrile phase prepared by the contact treatment A, 488 mL of water and 57.24 g of a 35 wt % aqueous sodium hydrogen sulfite solution were added, followed by stirring at 24° C. for 1 hour. Subsequently, the liquid was left to stand for separating into an isobutyronitrile phase and an aqueous phase, and the aqueous phase was removed (contact treatment B).

To the isobutyronitrile phase prepared by the contact treatment B, 488 mL of water, 34.34 g of a 35% aqueous sodium hydrogen sulfite solution, and 11.36 g of 35% hydrochloric acid were added. The mixture was heated up to 60° C. while blowing air into the gas phase at 10 mL/min and was left to stand at the same temperature for 1.5 hours. Then, cooling down to 24° C. and leaving to stand were performed for separating into an isobutyronitrile phase and an aqueous phase, and the aqueous phase was removed (contact treatment D).

To the isobutyronitrile phase prepared by the contact treatment D, 257 mL of water and a 25 wt % aqueous sodium hydroxide solution were added to adjust the pH to 11.1, followed by stirring at 24° C. for 0.5 hours. The liquid was left to stand for separating into an isobutyronitrile phase and an aqueous phase, and the aqueous phase was removed (contact treatment C).

To the isobutyronitrile phase prepared by the contact treatment C, 257 mL of water was added, followed by stirring at 24° C. for 0.5 hours. Subsequently, the liquid was left to stand for separating into an isobutyronitrile phase and an aqueous phase, and the aqueous phase was removed (water washing treatment).

The isobutyronitrile phase prepared by the water washing treatment was heat-refluxed for Dean-Stark dehydration. Subsequently, distillation was performed at the boiling point of isobutyronitrile (internal temperature: 108° C. or less) (distillation treatment). The impurities contained in the isobutyronitrile phase prepared by the distillation treatment were less than 2 ppm of N-isobutyl-2-methylpropane-1-imine, less than 2 ppm of isobutyl aldehyde, less than 2 ppm of 2,5-dimethylhexa-2,4-diene, and less than 2 ppm of N-isobutylformamide.

The invention claimed is:

1. A method for purifying a nitrile solvent, comprising:
   bringing the nitrile solvent containing at least an imine and a conjugated diene as impurities into contact with an acidic aqueous solution having a pH of 3 or less;
   bringing the nitrile solvent having been contacted with the acidic aqueous solution into contact with an aqueous sodium hydrogen sulfite solution;
   bringing the nitrile solvent having been contacted with the aqueous sodium hydrogen sulfite solution into contact with an alkaline aqueous solution; and
   bringing the nitrile solvent containing impurities, the nitrile solvent having been contacted with the acidic aqueous solution, the nitrile solvent having been contacted with the aqueous sodium hydrogen sulfite solution, or the nitrile solvent having been contacted with the alkaline aqueous solution, into contact with an oxidizing agent.

2. The method for purifying a nitrile solvent according to claim 1, further comprising distilling the nitrile solvent having been contacted with the alkaline aqueous solution.

3. The method for purifying a nitrile solvent according to claim 1, wherein the acidic aqueous solution is hydrochloric acid.

4. The method for purifying a nitrile solvent according to claim 1, wherein the alkaline aqueous solution is an aqueous sodium hydroxide solution.

5. The method for purifying a nitrile solvent according to claim 1, wherein the nitrile solvent is isobutyronitrile.

6. A method for purifying a nitrile solvent, comprising:
bringing a nitrile solvent containing at least an imine and a conjugated diene as impurities into contact with an acidic aqueous solution having a pH of 3 or less to convert the imine into a carbonyl compound;
subjecting the nitrile solvent having been contacted with the acidic aqueous solution to a treatment for removing the carbonyl compound; and
bringing the nitrile solvent containing impurities or the nitrile solvent having been contacted with the acidic aqueous solution into contact with an oxidizing agent to remove the conjugated diene.

7. The method for purifying a nitrile solvent according to claim 1, further comprising distilling the nitrile solvent having been contacted with the alkaline aqueous solution or the nitrile solvent having been contacted with the oxidizing agent.

8. The method for purifying a nitrile solvent according to claim 1, wherein the nitrile solvent containing impurities, the nitrile solvent having been contacted with the acidic aqueous solution, the nitrile solvent having been contacted with the aqueous sodium hydrogen sulfite solution, or the nitrile solvent having been contacted with the alkaline aqueous solution is brought into contact with the oxidizing agent at a temperature up to 60° C.

9. The method for purifying a nitrile solvent according to claim 6, wherein the nitrile solvent containing impurities or the nitrile solvent having been contacted with the acidic aqueous solution is brought into contact with the oxidizing agent at a temperature up to 60° C.

* * * * *